(12) United States Patent
Martens et al.

(10) Patent No.: US 8,561,614 B2
(45) Date of Patent: Oct. 22, 2013

(54) MULTI-LAYER CUFFS FOR MEDICAL DEVICES

(75) Inventors: Paul W. Martens, Pleasanton, CA (US); Joel C. Colburn, Walnut Creek, CA (US)

(73) Assignee: Covidien LP, Mansfield, MA (US)

( * ) Notice: Subject to any disclaimer, the term of this patent is extended or adjusted under 35 U.S.C. 154(b) by 1349 days.

(21) Appl. No.: 11/529,117

(22) Filed: Sep. 28, 2006

(65) Prior Publication Data

US 2008/0078400 A1 Apr. 3, 2008

(51) Int. Cl.
*A61M 16/00* (2006.01)
*A62B 9/06* (2006.01)

(52) U.S. Cl.
USPC .................................................... 128/207.14

(58) Field of Classification Search
USPC ................. 128/207, 207.15, 207.14, 200.26, 128/207.16–207.18, 200.24; 606/198, 192; 604/96.01
See application file for complete search history.

(56) References Cited

U.S. PATENT DOCUMENTS

| | | | |
|---|---|---|---|
| 2,927,584 A | 3/1960 | Wallace | |
| 3,810,474 A | 5/1974 | Cross | |
| 4,130,617 A * | 12/1978 | Wallace | 264/528 |
| 4,328,056 A * | 5/1982 | Snooks | 156/242 |
| 4,340,046 A | 7/1982 | Cox | |
| 4,417,576 A | 11/1983 | Baran | |
| 4,569,344 A | 2/1986 | Palmer | |
| 4,638,539 A | 1/1987 | Palmer | |
| 4,696,296 A | 9/1987 | Palmer | |
| 4,825,859 A | 5/1989 | Lambert | |
| 4,834,726 A | 5/1989 | Lambert | |
| 4,836,199 A | 6/1989 | Palmer | |
| 4,838,255 A | 6/1989 | Lambert | |
| 4,867,153 A | 9/1989 | Lorenzen et al. | |
| 4,872,579 A | 10/1989 | Palmer | |
| 4,927,412 A | 5/1990 | Menasche | |
| 4,938,741 A | 7/1990 | Lambert | |
| 4,963,313 A | 10/1990 | Noddin et al. | |
| 4,967,743 A | 11/1990 | Lambert | |
| 5,021,045 A | 6/1991 | Buckberg et al. | |
| 5,025,806 A | 6/1991 | Palmer et al. | |

(Continued)

FOREIGN PATENT DOCUMENTS

| | | |
|---|---|---|
| CA | 2353007 A1 | 6/2000 |
| DE | 19855521 A1 | 6/2000 |

(Continued)

OTHER PUBLICATIONS

U.S. Appl. No. 11/453,161, filed Jun. 14, 2006, Campbell, et al.

(Continued)

*Primary Examiner* — Justine Yu
*Assistant Examiner* — Colin W Stuart
(74) *Attorney, Agent, or Firm* — Fletcher Yoder, P.C.

(57) ABSTRACT

An inflatable cuff may be adapted to seal a vessel of a patient, such as a trachea when associated with a medical device, such as an endotracheal tube. In one embodiment, an inflatable cuff made from multiple layers is provided where one or more layers are chosen to improve sealing of the tube in the vessel. In exemplary embodiments, the individual layers may improve sealing by swelling in the presence of moisture, being wettable by the tissues of the trachea, or both. In one implementation, the inflatable cuff may be made of any combination of layers that perform either or both of these functions.

22 Claims, 3 Drawing Sheets

(56) References Cited

U.S. PATENT DOCUMENTS

| | | |
|---|---|---|
| 5,029,580 A | 7/1991 | Radford et al. |
| 5,060,646 A | 10/1991 | Page |
| 5,065,754 A | 11/1991 | Jensen |
| 5,098,379 A | 3/1992 | Conway et al. |
| 5,103,816 A | 4/1992 | Kirschbaum et al. |
| 5,107,829 A | 4/1992 | Lambert |
| 5,120,322 A | 6/1992 | Davis et al. |
| 5,122,122 A | 6/1992 | Allgood |
| 5,133,345 A | 7/1992 | Lambert |
| 5,135,516 A | 8/1992 | Sahatjian et al. |
| 5,137,671 A | 8/1992 | Conway et al. |
| 5,158,569 A | 10/1992 | Strickland et al. |
| 5,165,420 A | 11/1992 | Strickland |
| 5,190,810 A | 3/1993 | Kirschbaum et al. |
| 5,199,427 A | 4/1993 | Strickland |
| 5,207,643 A | 5/1993 | Davis |
| 5,215,522 A | 6/1993 | Page et al. |
| 5,218,957 A | 6/1993 | Strickland |
| 5,230,332 A | 7/1993 | Strickland |
| 5,233,979 A | 8/1993 | Strickland |
| 5,246,012 A | 9/1993 | Strickland |
| 5,250,070 A | 10/1993 | Parodi |
| 5,261,896 A | 11/1993 | Conway et al. |
| 5,263,478 A | 11/1993 | Davis |
| 5,269,770 A | 12/1993 | Conway et al. |
| 5,277,177 A | 1/1994 | Page et al. |
| 5,304,121 A | 4/1994 | Sahatjian |
| 5,360,402 A | 11/1994 | Conway et al. |
| 5,370,656 A | 12/1994 | Shevel |
| 5,370,889 A | 12/1994 | Fortuin et al. |
| 5,374,261 A | 12/1994 | Yoon |
| 5,392,787 A | 2/1995 | Yoon |
| 5,397,302 A | 3/1995 | Weaver et al. |
| 5,407,423 A | 4/1995 | Yoon |
| 5,423,745 A | 6/1995 | Todd et al. |
| 5,439,457 A | 8/1995 | Yoon |
| 5,447,505 A | 9/1995 | Valentine et al. |
| 5,451,204 A | 9/1995 | Yoon |
| 5,452,715 A * | 9/1995 | Boussignac ............ 128/207.15 |
| 5,466,231 A | 11/1995 | Cercone et al. |
| 5,469,864 A | 11/1995 | Rosenblatt |
| 5,482,740 A | 1/1996 | Conway et al. |
| 5,484,426 A | 1/1996 | Yoon |
| 5,487,730 A | 1/1996 | Marcadis et al. |
| 5,494,029 A | 2/1996 | Lane et al. |
| 5,501,669 A | 3/1996 | Conway et al. |
| 5,507,284 A | 4/1996 | Daneshvar |
| 5,524,642 A | 6/1996 | Rosenblatt |
| 5,545,132 A | 8/1996 | Fagan et al. |
| 5,556,391 A | 9/1996 | Cercone et al. |
| 5,593,718 A | 1/1997 | Conway et al. |
| 5,599,292 A | 2/1997 | Yoon |
| 5,599,299 A | 2/1997 | Weaver et al. |
| 5,599,321 A | 2/1997 | Conway et al. |
| 5,611,336 A | 3/1997 | Page et al. |
| 5,613,950 A | 3/1997 | Yoon |
| 5,649,902 A | 7/1997 | Yoon |
| 5,670,111 A | 9/1997 | Conway et al. |
| 5,674,192 A | 10/1997 | Sahatjian et al. |
| 5,694,922 A | 12/1997 | Palmer |
| 5,700,239 A | 12/1997 | Yoon |
| 5,715,815 A | 2/1998 | Lorenzen et al. |
| 5,720,726 A | 2/1998 | Marcadis et al. |
| 5,722,931 A | 3/1998 | Heaven |
| 5,730,123 A | 3/1998 | Lorenzen |
| 5,733,252 A | 3/1998 | Yoon |
| 5,735,271 A | 4/1998 | Lorenzen et al. |
| 5,765,559 A | 6/1998 | Kim |
| 5,810,786 A | 9/1998 | Jackson et al. |
| 5,827,215 A | 10/1998 | Yoon |
| 5,843,017 A | 12/1998 | Yoon |
| 5,843,028 A | 12/1998 | Weaver et al. |
| 5,843,060 A | 12/1998 | Cercone |
| 5,843,089 A | 12/1998 | Sahatjian et al. |
| 5,868,719 A | 2/1999 | Tsukernik |
| 5,954,706 A | 9/1999 | Sahatjian |
| 5,954,740 A | 9/1999 | Ravenscroft et al. |
| 5,971,954 A | 10/1999 | Conway et al. |
| 5,997,503 A | 12/1999 | Willis et al. |
| 5,997,546 A | 12/1999 | Foster et al. |
| 6,010,480 A | 1/2000 | Abele et al. |
| 6,012,451 A | 1/2000 | Palmer |
| 6,048,332 A | 4/2000 | Duffy et al. |
| 6,110,192 A | 8/2000 | Ravenscroft et al. |
| 6,129,547 A | 10/2000 | Cise |
| 6,132,824 A | 10/2000 | Hamlin |
| 6,169,123 B1 | 1/2001 | Cercone |
| 6,210,364 B1 | 4/2001 | Anderson |
| 6,214,895 B1 | 4/2001 | Cercone |
| 6,227,200 B1 | 5/2001 | Crump et al. |
| 6,240,321 B1 | 5/2001 | Janke et al. |
| 6,248,088 B1 | 6/2001 | Yoon |
| 6,264,631 B1 | 7/2001 | Willis et al. |
| 6,264,633 B1 | 7/2001 | Knorig |
| 6,277,089 B1 | 8/2001 | Yoon |
| 6,312,421 B1 | 11/2001 | Boock |
| 6,322,586 B1 | 11/2001 | Monroe et al. |
| 6,364,856 B1 | 4/2002 | Ding et al. |
| 6,394,093 B1 | 5/2002 | Lethi |
| 6,395,012 B1 | 5/2002 | Yoon et al. |
| 6,398,266 B1 | 6/2002 | Crump |
| 6,409,716 B1 | 6/2002 | Sahatjian et al. |
| 6,494,203 B1 | 12/2002 | Palmer |
| 6,524,274 B1 | 2/2003 | Rosenthal et al. |
| 6,526,977 B1 | 3/2003 | Göbel |
| 6,543,451 B1 | 4/2003 | Crump et al. |
| 6,551,272 B2 | 4/2003 | Göbel |
| 6,572,813 B1 | 6/2003 | Zhang et al. |
| 6,584,970 B1 | 7/2003 | Crump et al. |
| 6,588,425 B2 | 7/2003 | Rouns et al. |
| 6,588,427 B1 | 7/2003 | Carlsen et al. |
| 6,602,218 B2 | 8/2003 | Yoon |
| 6,602,219 B2 | 8/2003 | Madsen et al. |
| 6,609,520 B1 | 8/2003 | Carlsen et al. |
| 6,612,304 B1 | 9/2003 | Cise et al. |
| 6,613,025 B1 | 9/2003 | Palasis |
| 6,615,835 B1 | 9/2003 | Cise et al. |
| 6,620,128 B1 | 9/2003 | Simhambhatla |
| 6,623,450 B1 | 9/2003 | Dutta |
| 6,629,530 B2 | 10/2003 | Cise |
| 6,632,091 B1 | 10/2003 | Cise et al. |
| 6,651,664 B1 | 11/2003 | Lomholt |
| 6,688,306 B1 | 2/2004 | Cise et al. |
| 6,698,424 B2 | 3/2004 | Madsen et al. |
| 6,726,696 B1 | 4/2004 | Houser et al. |
| 6,745,773 B1 | 6/2004 | Gobel |
| 6,767,340 B2 | 7/2004 | Willis et al. |
| 6,769,430 B1 | 8/2004 | Carlsen et al. |
| 6,770,066 B1 | 8/2004 | Leighton et al. |
| 6,786,876 B2 | 9/2004 | Cox |
| 6,790,221 B2 | 9/2004 | Monroe et al. |
| 6,802,317 B2 | 10/2004 | Göbel |
| 6,805,125 B1 | 10/2004 | Crump et al. |
| 6,808,521 B1 | 10/2004 | McMichael |
| 6,908,449 B2 | 6/2005 | Willis et al. |
| 6,916,307 B2 | 7/2005 | Willis et al. |
| 6,923,786 B2 | 8/2005 | Rouns et al. |
| 6,997,918 B2 | 2/2006 | Soltesz et al. |
| 7,040,321 B2 | 5/2006 | Göbel |
| 7,096,868 B2 | 8/2006 | Tateo et al. |
| 2001/0041861 A1 | 11/2001 | Gobel |
| 2002/0077603 A1 | 6/2002 | Willis et al. |
| 2002/0077604 A1 | 6/2002 | Willis et al. |
| 2002/0078960 A1 | 6/2002 | Cise |
| 2002/0078963 A1 | 6/2002 | Rouns et al. |
| 2002/0082552 A1 | 6/2002 | Ding et al. |
| 2002/0091375 A1 | 7/2002 | Sahatjian et al. |
| 2002/0193753 A1 | 12/2002 | Rouns et al. |
| 2003/0000526 A1 | 1/2003 | Gobel |
| 2003/0032407 A1 | 2/2003 | Mages |
| 2003/0066532 A1 | 4/2003 | Gobel |
| 2003/0069620 A1 | 4/2003 | Li |
| 2003/0111077 A1 | 6/2003 | Hooser et al. |
| 2003/0116162 A1 | 6/2003 | Madsen et al. |

(56) References Cited

U.S. PATENT DOCUMENTS

| | | |
|---|---|---|
| 2003/0116963 A1 | 6/2003 | Teuscher et al. |
| 2003/0225369 A1 | 12/2003 | McMichael et al. |
| 2003/0225392 A1 | 12/2003 | McMichael et al. |
| 2003/0225393 A1 | 12/2003 | McMichael et al. |
| 2004/0024363 A1 | 2/2004 | Goldberg |
| 2004/0079376 A1 | 4/2004 | Melker |
| 2004/0092870 A1 | 5/2004 | Squire et al. |
| 2004/0106899 A1 | 6/2004 | McMichael et al. |
| 2004/0106900 A1 | 6/2004 | Triebes et al. |
| 2004/0106901 A1 | 6/2004 | Letson et al. |
| 2004/0122110 A1* | 6/2004 | MacCabee et al. ............ 514/725 |
| 2004/0193100 A1 | 9/2004 | Van Hooser et al. |
| 2004/0193101 A1 | 9/2004 | Van Hooser et al. |
| 2004/0215142 A1 | 10/2004 | Matheis et al. |
| 2004/0220534 A1* | 11/2004 | Martens et al. ............... 604/265 |
| 2004/0255952 A1 | 12/2004 | Carlsen et al. |
| 2005/0004560 A1 | 1/2005 | Cox |
| 2005/0033267 A1 | 2/2005 | Decaria |
| 2005/0033268 A1 | 2/2005 | Decaria |
| 2005/0033269 A1 | 2/2005 | Decaria |
| 2005/0038381 A1 | 2/2005 | McMichael |
| 2005/0065468 A1 | 3/2005 | Goebel |
| 2005/0124932 A1 | 6/2005 | Foster et al. |
| 2005/0124935 A1 | 6/2005 | McMichael |
| 2006/0118121 A1 | 6/2006 | Martens et al. |
| 2006/0118122 A1 | 6/2006 | Martens et al. |
| 2008/0125711 A1* | 5/2008 | Alpini et al. ............. 604/103.06 |

FOREIGN PATENT DOCUMENTS

| | | |
|---|---|---|
| EP | 0214721 A1 | 3/1987 |
| EP | 1005877 A2 | 6/2000 |
| EP | 1135184 | 6/2000 |
| EP | 1267981 B1 | 1/2003 |
| GB | 1313347 A1 | 4/1973 |
| WO | WO 2007140262 A1 | 4/1973 |
| WO | WO 00/32262 A1 | 6/2000 |
| WO | WO 03/045487 A2 | 6/2003 |
| WO | WO 2004/101046 A1 | 11/2004 |
| WO | WO 2007149202 A1 | 12/2007 |

OTHER PUBLICATIONS

U.S. Appl. No. 11/472,915, filed Jun. 22, 2006, Morris, et al.
U.S. Appl. No. 11/473,362, filed Jun. 22, 2006, Nelson.
U.S. Appl. No. 11/472,733, filed Jun. 22, 2006, Nelson.
U.S. Appl. No. 11/473,285, filed Jun. 22, 2006, Colburn, et al.
U.S. Appl. No. 11/527,070, filed Sep. 26, 2006, Flagler.
Tecogel brochure page, Noveon Thermedics Polymer Products, Oct. 2003.
International Search Report PCT/US2007/020376, 5 pages, mailed Dec. 2, 2008.

* cited by examiner

MULTI-LAYER CUFFS FOR MEDICAL DEVICES

BACKGROUND OF THE INVENTION

1. Field of the Invention

The present invention relates to medical devices, and more particularly, to airway products, such as tracheal tubes and cuffs.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into the patient. For example, medical devices such as tracheal tubes may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes or tracheostomy tubes. To seal these types of tracheal tubes, an inflatable cuff may be associated with these tubes. When inflated, the cuff generally expands to contact the trachea walls to seal the tracheal passage around the tube.

However, to fit a range of trachea anatomies and to provide low intra cuff pressure, cuff diameters are usually about one and a half times the diameter of the average trachea. Therefore, when inserted in an average-sized trachea, such a cuff is unable to fully expand and will fold in on itself within the trachea. These folds may serve as leak paths that allow mucosal secretions to flow past the cuff and enter the lung.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

One embodiment provides an inflatable cuff mounted on a core structure. The inflatable cuff is made from at least two layers, at least one of which enhances sealing of the inflatable cuff to the walls of a vessel.

Another embodiment provides an inflatable cuff configured to be mounted on a core structure. The inflatable cuff is made from at least two layers, at least one of which enhances sealing of the inflatable cuff to the walls of a vessel.

Another embodiment provides a method of manufacturing a medical device by forming a multi-layer tube of at least two layers, at least one of which enhances sealing of an inflatable cuff to the walls of a vessel. The method is completed by feeding the multi-layer tube into a blow molding apparatus, blowing a series of inflatable cuffs in the multi-layer tube, and cutting the multi-layer tube into segments, so that each segment contains an inflatable cuff configured to be mounted on a core structure.

Another embodiment provides a method of manufacturing a medical device by mounting an inflatable cuff, made from at least two layers, at least one of which enhances sealing of the inflatable cuff to the walls of a vessel, onto a core structure.

Another embodiment provides a method of sealing a medical device against a vessel wall, by placing a tube with a mounted inflatable cuff, made from at least two layers, at least one of which enhances sealing of the inflatable cuff to the walls of a vessel, into a vessel in a body, and inflating the multi-layer inflatable cuff to contact the walls of the vessel.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide an inflatable cuff for mounting on a device, such as an endotracheal tube or other medical device, which may substantially seal the passage in which the tube is inserted. For example, sealing an endotracheal tube to the trachea enables mechanical ventilation to be implemented, so that air, oxygen, or medications may be introduced into the lungs. In accordance with some aspects of the invention, an inflatable cuff, designed to be mounted on a medical device is provided. The inflatable cuff is made from at least two layers, and includes proximal and distal openings through which a core structure can be passed.

The multi-layer inflatable cuff described herein provides advantages over a typical, single layer, cuff. A typical inflatable cuff generally assumes a cylindrical or barrel shape when inflated that may include short tapered or partially tapered sections designed to connect the ends of the cuff to a narrower object, such as an endotracheal tube. Thus, a generally cylindrical cuff has a constant diameter along most of its length when fully inflated. This diameter is typically larger than the size of the tracheal passage. Therefore, when a typical cylindrical cuff is inserted into a patient's trachea and inflated, the cuff walls of the cylinder are unable to inflate to their maximum diameter and may fold in on themselves, which may cause wrinkles and leak paths to form.

A multi-layer cuff provides an improved seal to a patient's trachea. In the multi-layer cuff, some layers are chosen for strength, allowing for production and use of the cuff, while other layers are chosen to provide improved sealing characteristics for sealing against a vessel wall. For example, one or more layers of the multi-layer cuff may be chosen to swell upon contact with moisture, thereby plugging wrinkles and enhancing the sealing of the cuff, or to be wettable against the side of the vessel walls.

Figure 1:
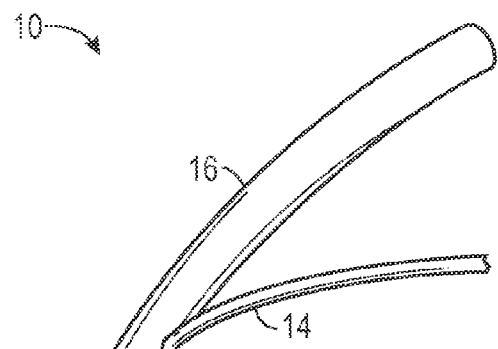
FIG. 1 illustrates an endotracheal tube with a multi-layer cuff in accordance with aspects of the present technique.
Figure 1:
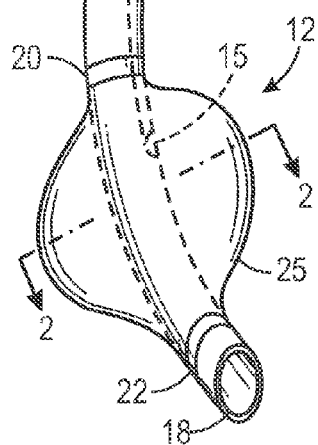

Turning to the figures, FIG. 1 illustrates an example of a multi-layer inflatable cuff used in conjunction with a medical device. The cuffed endotracheal tube 10 includes a multi-layer cuff 12 that may be inflated to form a seal against the tracheal wall 30 (see FIG. 3). The multi-layer cuff 12 is disposed on an endotracheal tube 16 that is suitably sized and shaped to be inserted into a patient and allow the passage of air through the endotracheal tube 16. Typically the cuff is disposed, adhesively or otherwise, towards the distal end 18 of the endotracheal tube 16. The multi-layer cuff 12 may be inflated and deflated via a lumen 14 in communication with the multi-layer cuff 12, typically through a hole or notch 15 in the lumen 14. The multi-layer cuff 12 may generally have an amorphous or irregular shape when not inflated, but may assume a shape generally corresponding to the vessel in which it is to be inserted when inflated. The multi-layer cuff 12 has a proximal opening 20 and a distal opening 22 formed in the cuff walls 25. These openings are sized to accommodate the endotracheal tube 16, the proximal opening 20 located closer to the machine end of the tube 16, and a distal opening 22 located closer to the distal end 18 of the tube 16.

Figure 2:
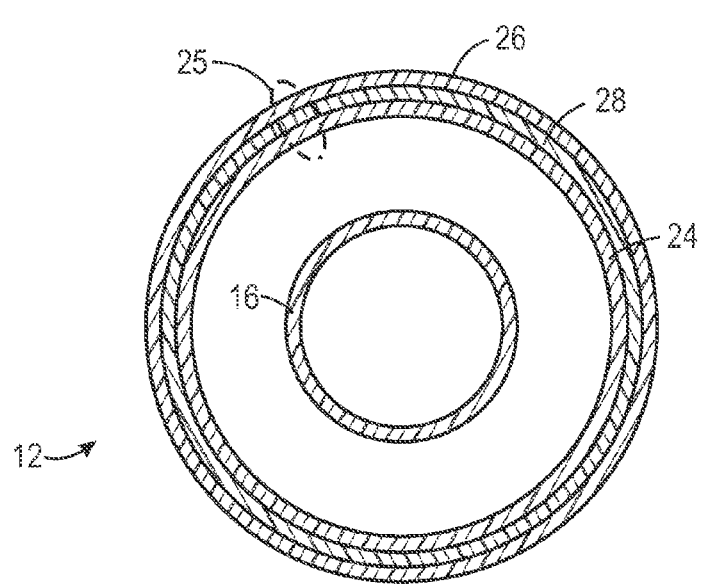
FIG. 2 illustrates a cross section of the multi-layer structure.

FIG. 2 illustrates a cross-section of the multi-layer cuff 12 in the fully inflated configuration. An endotracheal tube 16 is shown in the center, while the structure of the wall 25 of the multi-layer cuff 12 is shown by the outside layers. The innermost layer 24 of the multi-layer cuff 12 may be formed from materials having suitable mechanical properties for the particular layers involved, such as puncture resistance, pinhole resistance, chemical bonding, and melt strength for blow molding. Examples of polymers that the innermost layer could be made from include, but are not limited to, polyethylene teraphthalate (PET), polyethylene, polyvinyl chloride (PVC), silicone, neoprene, polyisoprene, polypropylene, polyurethane (PU), or any appropriate blends of these polymers.

The outermost layer 26 may be formed from materials having suitable physical and chemical properties for direct contact with tissue, such as swelling, wettability, or softening to prevent leaks, biocompatibility, and the ability to function as a drug delivery system. While this layer may be a polymeric material, it does not have to be. Any other appropriate composition that can be formed with the other layers, such as by co-extrusion, and yet has the physical strength and chemical durability to endure the processing steps and insertion into a passage, such as the trachea (see FIG. 3), without degradation or removal could be used. Examples of materials that could be used for the outermost layer include, but are not limited to, hydroxypropyl methyl cellulose, carboxy methyl cellulose, hydroscopic polyurethane, polyethylene oxide, hydroscopic polyacrylamide, hydroscopic polyester, polysiloxane, polyvinyl alcohol, poly(vinyl pyrrolidone), poly(ethylene-co-vinyl acetate), polylactide, polyglycolide, hydroscopic poly (N-vinyl lactam), polypeptide, or any appropriate blends of these materials. In one embodiment, the innermost layer 24 of the wall 25 of the inflatable cuff 12 is made of a polyvinyl chloride having suitable mechanical and chemical properties, while the outermost layer 26 is made from a polyethylene oxide.

One or more interior layers 28 may also be included to improve the lamination strength between the other layers. Since the layers in the overall structure are chosen for specific functions, it may contain more then three layers, and possible structures containing five or seven layers are conceivable. In these more complex structures, multiple interior layers 28 may also be used, for example, in the second and fourth layers of a five layer structure. Optionally, a interior layer 28 that swells upon absorbing moisture may be used to assist in sealing the multi-layer cuff to the trachea wall 30 (see FIG. 5).

Multi-layer cuff structures also permit the addition of pharmaceutically active compounds in one or more of the layers. Materials may be selected for the outermost layer 26 or an interior layer 28 that are permeable, allowing added pharmaceuticals to diffuse out into the surrounding tissues, either all at once or over a timed release period. Material selection may also be made on the basis of chemical compatibility with the targeted pharmaceutical. In an exemplary embodiment, forming the cuff 12 by co-extrusion allows for shorter exposure to high temperatures in some layers, which may protect pharmaceutically active compounds from degradation. Examples of types of pharmaceutically active compounds that may be chosen include, but are not limited to, antimicrobial compounds, mucosal regenerative compounds, anti-inflammatory compounds, cilia regenerative compounds, or combinations of these compounds. In these exemplary embodiments, mucosal and cilia regenerative compounds may include substances such as FGF (fibroblast growth factor), EGF (epidermal growth factor), PDGF (platelet-derived growth factor), IGF (insulin-like growth factor), TGF-$\beta$1 through 3, cytokines, interferons, interleukins; hormones, insulin, growth hormone-releasing factor, calcitonin, and/or vitamins such as vitamin C, vitamin E, vitamin A or retinoic acid (e.g. trans-retinoic acid, 13-cis-retinoic acid, 9-cis-retinoic acid, other retinoids and mixtures thereof).

Figure 3:
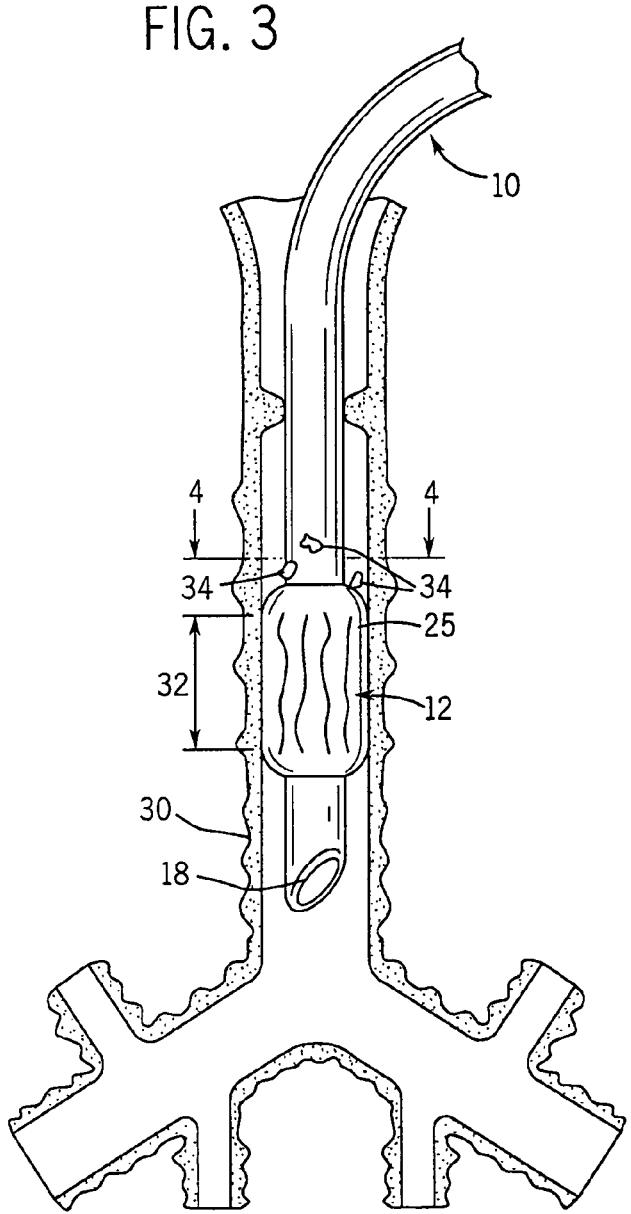
FIG. 3 illustrates the inflatable balloon cuff of the present techniques inserted into a patient's trachea.

FIG. 3 shows the exemplary cuffed endotracheal tube 10 inserted into a patient's trachea. The multi-layer cuff 12 is inflated to form a seal against the tracheal walls 30. Since the diameter of the cuff is larger than the diameter of the trachea, inflation results in wrinkles forming in a zone 32 around the largest circumference of the multi-layer cuff 12. These wrinkles may result in the leakage of secretions 34 or other detritus materials past the multi-layer cuff 12. To prevent this, one or more layers of the multi-layer cuff 12, such as outermost layer 26 or an interior layer 28, may swell when in contact with the moist tissues of the patient's trachea, while the outmost layer 26 (see FIG. 2) may remain moist to improve the seal to the trachea wall, as described in more detail in FIG. 5.

Figure 4:
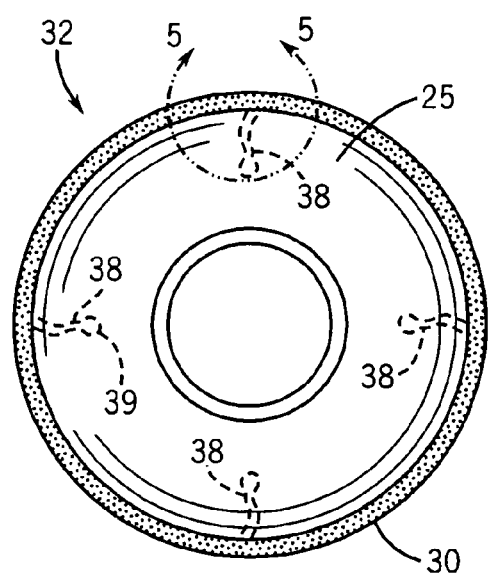
FIG. 4 illustrates a top view of the folds in the wrinkled region of the balloon cuff of FIG. 3.

FIG. 4 depicts a top view of a cross-section taken along view line 4 in FIG. 3, looking down at an inserted multi-layer cuff 12. As depicted, the cuff walls 25 are unable to inflate to their fully inflated diameters in the tracheal passage. In order to fit it into the passage, the flexible cuff walls 25 of the multi-layer cuff 12 fold in on each other and may form multiple wrinkles 38. The innermost tip of each wrinkle 38 may form a radius or circumference, providing a channel 39 through the cuff.

Figure 5:
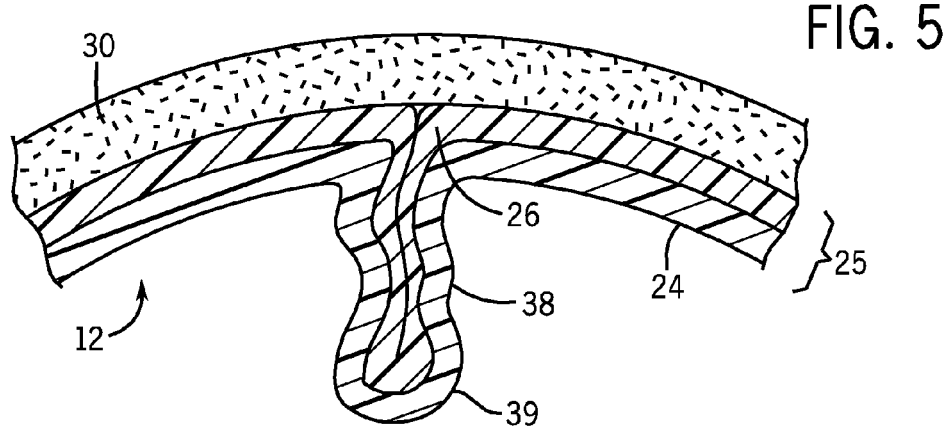
FIG. 5 illustrates a close-up view of the multi-layer structure in contact with the walls of the trachea, showing the swollen outermost layer sealing a fold in the balloon cuff.

As depicted in FIG. 5, such channels 39 are partially or completely blocked in an exemplary embodiment. In the depicted exemplary embodiment, FIG. 5 illustrates the sealing of the multi-layer cuff 12 to the trachea walls. In this example, the outermost layer 26 of the wall 25 of the multi-layer cuff 12 swells in the presence of moisture from the tracheal wall 30 to seal a wrinkle 38. As depicted, the swollen outermost layer 26 substantially fills the wrinkles 38 and channels 39 such that secretions 34 and detritus cannot pass the multi-layer cuff 12 via the wrinkles 38 or through the channels 39. In an alternative embodiment, an interior layer 28 may swell and fill the wrinkles 38 and channels 39, either in addition to, or instead of, swelling of the outermost layer 26.

The outermost layer 26 may also be wettable by the trachea wall 30, providing a better seal. In an exemplary embodiment, surface tension between the trachea wall 30 and the wetted outermost layer 26 improves the seal between the trachea wall 30 and the multi-layer cuff 12. Those skilled in the art will recognize that this is not the only mechanism by which the multi-layer cuff 12 may seal to the trachea wall 30. FIG. 5 also shows an innermost layer 24 surrounding the swollen outermost layer and providing strength to the multi-layer cuff 12.

Figure 6:
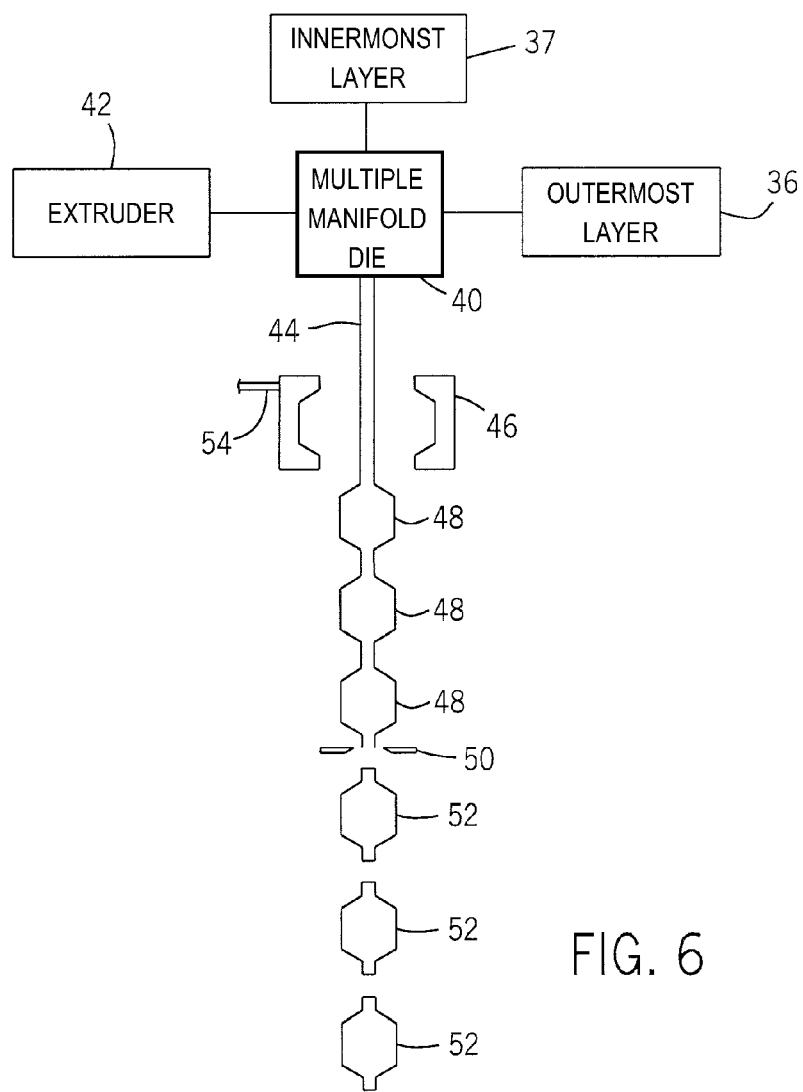
FIG. 6 illustrates a flowchart depicting a blow molding method of manufacturing a balloon cuff of the present techniques.

FIG. 6 illustrates one example of a production system for the individual multi-layer cuffs. In this example, an extruder for the outermost layer 36 feeds a melt into a multiple manifold die 40 for tubing formation. The extruder for the innermost layer 37 feeds a polymer melt into the multiple manifold die 40 for forming the innermost layer 24 simultaneously with the formation of the outermost layer 26. An optional extruder 42 can be used to form an interior layer 28 between the inner layer and the outer layer, such as to improve the lamination strength between these two layers. The multi-layer tube 44 formed in the multiple manifold die 40 is fed from the multiple manifold die 40 into a blow mold 46 where air 54 is used to inflate the tube against the hot walls of the mold 46 forming an inflatable cuff 48 in the multilayer tube 44. Multiple inflated cuffs 48 are sequentially formed in the multi-layer tube 44. This multi-layer tube 44 with the multiple inflatable cuffs 48 is then fed into a cutter 50, which cuts the multiple inflatable cuffs 48 into individual multi-layer inflatable cuffs 52 ready for mounting on the endotracheal tube 16 (see FIG. 1).

In addition to co-extrusion, other systems for forming the multi-layer cuff 12 may be used. These include techniques such as dip coating a tube of the innermost layer 24, with a melt or a solution of the outermost layer 26, to form the multi-layer tube 44, followed by blow molding the tube as shown in FIG. 6. An interior layer 28 could optionally be included, either by an additional dip-coating step, or by co-extrusion with the innermost layer 24 prior to dip coating the outermost layer 26. Another technique that could be used would involve injection blow molding to form the multi-layer cuffs 52 directly. Those skilled in the art will recognize that other techniques may also be used to form these structures.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to sealing endotracheal tubes, but these techniques may also be utilized for the sealing of other medical devices inserted into passages in the body. Rather, the invention is to cover all modifications, equivalents, and alternatives falling within the spirit and scope of the invention as defined by the following appended claims.

What is claimed is:

1. A medical device comprising:
an inflatable cuff mounted on a core structure, wherein the inflatable cuff comprises at least two layers coextensive with each other such that the at least two layers inflate and deflate concurrently, wherein one of the at least two layers comprises an outermost layer of the inflatable cuff that swells upon absorbing moisture and wherein the core structure comprises a tracheal tube; and comprising an interior layer coextensive with the at least two layers and disposed between the at least two layers.

2. The medical device of claim 1, wherein at least one layer comprises at least one of a polyethylene teraphthalate (PET), a polyethylene, a polyvinyl chloride (PVC), a silicone, a neoprene, a polyisoprene, a polypropylene, a polyurethane (PU).

3. The medical device of claim 1, wherein at least one layer comprises at least one of a hydroxypropyl methyl cellulose, a carboxy methyl cellulose, a hydroscopic polyurethane, a polyethylene oxide, a hydroscopic polyacrylamide, a hydroscopic polyester, a polysiloxane, a polyvinyl alcohol, a poly(vinyl pyrrolidone), a poly(ethylene-co-vinyl acetate), a polylactide, a polyglycolide, a hydroscopic poly(N-vinyl lactam), a polypeptide.

4. The medical device of claim 1, comprising a pharmaceutically active compound in at least one of the layers.

5. The medical device of claim 4, wherein the pharmaceutically active compound comprises at least one of an antimicrobial compound, a mucosal regenerative compound, an mid-inflammatory compound, a cilia regenerative compound.

6. A medical device comprising:
an inflatable cuff configured to be mounted on a tracheal tube, wherein the inflatable cuff comprises at least two layers, wherein a first layer folds in on itself upon inflation against a tracheal wall to form a wrinkle or a channel and an outermost layer swells upon absorbing moisture to substantially fill the wrinkle or the channel; wherein the inflatable cuff comprises an interior layer disposed between the at least two layers to improve the lamination strength of adjacent layers.

7. The medical device of claim 6, wherein at least one layer comprises at least one of a polyethylene teraphthalate (PET), a polyethylene, a polyvinyl chloride (PVC), a silicone, a neoprene, a polyisoprene, a polypropylene, a polyurethane (PU).

8. The medical device of claim 6, wherein at least one layer comprises at least one of a hydroxypropyl methyl cellulose, a carboxy methyl cellulose, a hydroscopic polyurethane, a polyethylene oxide, a hydroscopic polyacrylamide, a hydroscopic polyester, a polysiloxane, a polyvinyl alcohol, a poly(vinyl pyrrolidone), a poly(ethylene-co-vinyl acetate), a polylactide, a polyglycolide, a hydroscopic poly (N-vinyl lactam), a polypeptide.

9. The medical device of claim 6, comprising a pharmaceutically active compound in one of the layers.

10. The medical device of claim 9, wherein the pharmaceutically active compound comprises at least one of an antimicrobial compound, a mucosal regenerative compound, an anti-inflammatory compound, a cilia regenerative compound.

11. A method of manufacturing a medical device comprising the steps of:
forming a multi-layer tube comprising at least one layer of the multi-layer tube that swells upon absorbing moisture and is configured to be an outermost layer;
feeding the multi-layer tube into a blow molding apparatus;

blowing a series of inflatable cuffs in the multi-layer tube; and cutting the multi-layer tube into segments, wherein each segment contains an inflatable cuff configured to be mounted on a tracheal tube;

wherein the multi-layer tube comprises at least one interior layer disposed between at least two layers of the multi-layer tube to improve the lamination strength of adjacent layers.

12. The method of claim 11, wherein forming the multi-layer tube comprises co-extruding the layers.

13. The method of claim 11, wherein thrilling the multi-layer tube comprises dip-coating a tube to form additional layers.

14. The method of claim 11, wherein at least one layer of the multi-layer tube comprises at least one of a polyethylene teraphthalate (PET), a polyethylene, a polyvinyl chloride (PVC), a silicone, a neoprene, a polyisoprene, a polypropylene, a polyurethane (PU).

15. The method of claim 11, wherein at least one layer of the multi-layer tube comprises at least one of a hydroxypropyl methyl cellulose, a carboxy methyl cellulose, a hydroscopic polyurethane, a polyethylene oxide, a hydroscopic polyacrylamide, a hydroscopic polyester, a polysiloxane, a polyvinyl alcohol, a poly(vinyl pyrrolidone), a poly(ethylene-co-vinyl acetate), a polylactide, a polyglycolide, a hydroscopic poly (N-vinyl lactam), a polypeptide.

16. A method of manufacturing a medical device, comprising:

mounting an inflatable cuff onto a tracheal tube, wherein the inflatable cuff comprises at least two layers coextensive with each other such that the at least two layers inflate and deflate concurrently, wherein one of the at least two layers comprises an outermost layer of the inflatable cuff that swells upon absorbing moisture;

wherein the inflatable cuff comprises an interior layer coextensive with the at least two layers and disposed between the at least two layers to improve the lamination strength of adjacent layers.

17. The method of claim 16, wherein at least one layer comprises at least one of a polyethylene teraphthalate (PET), a polyethylene, a polyvinyl chloride (PVC), a silicone, a neoprene, a polyisoprene, a polypropylene, a polyurethane (PU).

18. The method of claim 16, wherein at least one layer comprises at least one of a hydroxypropyl methyl cellulose, a carboxy methyl cellulose, a hydroscopic polyurethane, a polyethylene oxide, a hydroscopic polyacrylamide, a hydroscopic polyester, a polysiloxane, a polyvinyl alcohol, a poly (vinyl pyrrolidone), a poly(ethylene-co-vinyl acetate), a polylactide, a polyglycolide, a hydroscopic poly (N-vinyl lactam), a polypeptide.

19. The method of claim 16, wherein the inflatable cuff comprises at least one layer comprising a pharmaceutically active compound.

20. The method of claim 19, wherein the pharmaceutically active compound comprises at least one of an antimicrobial compound, a mucosal regenerative compound, an anti-inflammatory compound, a cilia regenerative compound.

21. A method of sealing a medical device against a vessel wall, comprising the steps of placing a tube with an inflatable cuff mounted thereon, into a trachea in a body, wherein the inflatable cuff comprises at least two layers coextensive with each other such that the at least two layers inflate and deflate concurrently, and wherein at least one of the at least two layers comprises an outermost layer of the inflatable cuff that swells upon absorbing moisture; and inflating the inflatable cuff to contact the walls of the trachea;

and wherein the inflatable cuff comprises at least one interior layer disposed between the at least two layers of the inflatable cuff to improve lamination strength of adjacent layers.

22. The method of claim 21, comprising selecting the tube based on the presence of a pharmaceutically active compound in one of the layers.

* * * * *